US011253604B2

(12) United States Patent
Chung et al.

(10) Patent No.: US 11,253,604 B2
(45) Date of Patent: Feb. 22, 2022

(54) CONJUGATE OF METHOTREXATE AND PEPTIDE

(71) Applicant: CAREGEN CO., LTD., Anyang-si (KR)

(72) Inventors: Yong Ji Chung, Seoul (KR); Eun Mi Kim, Yongin-si (KR); Seon Soo Kim, Gunpo-si (KR)

(73) Assignee: Caregen Co., Ltd., Anyang-si (KR)

( * ) Notice: Subject to any disclaimer, the term of this patent is extended or adjusted under 35 U.S.C. 154(b) by 0 days.

(21) Appl. No.: 16/612,162

(22) PCT Filed: May 11, 2018

(86) PCT No.: PCT/KR2018/005448
§ 371 (c)(1),
(2) Date: Nov. 8, 2019

(87) PCT Pub. No.: WO2018/208125
PCT Pub. Date: Nov. 15, 2018

(65) Prior Publication Data
US 2021/0236648 A1    Aug. 5, 2021

(30) Foreign Application Priority Data

May 11, 2017    (KR) .................. 10-2017-0058867

(51) Int. Cl.
| A61K 47/64 | (2017.01) |
| A61K 31/519 | (2006.01) |
| A61P 29/00 | (2006.01) |
| A61K 9/00 | (2006.01) |
| A61K 9/08 | (2006.01) |
| A61K 9/20 | (2006.01) |
| A61K 9/48 | (2006.01) |
| A61K 9/16 | (2006.01) |

(52) U.S. Cl.
CPC ............ *A61K 47/64* (2017.08); *A61K 9/0019* (2013.01); *A61K 9/08* (2013.01); *A61K 9/1623* (2013.01); *A61K 9/1652* (2013.01); *A61K 9/1664* (2013.01); *A61K 9/2013* (2013.01); *A61K 9/2018* (2013.01); *A61K 9/2059* (2013.01); *A61K 9/4858* (2013.01); *A61K 9/4866* (2013.01); *A61K 31/519* (2013.01); *A61P 29/00* (2018.01)

(58) Field of Classification Search
CPC .... A61K 31/519; A61K 47/64; A61K 9/0019; A61K 9/08; A61K 9/1623; A61K 9/1652; A61K 9/1664; A61K 9/2013; A61K 9/2018; A61K 9/2059; A61K 9/4858; A61K 9/4866; A61P 29/00
See application file for complete search history.

(56) References Cited

U.S. PATENT DOCUMENTS

| 8,067,376 B2 * | 11/2011 | Lee .................. A61P 37/06 |
| | | 514/21.6 |
| 8,541,182 B2 | 9/2013 | Fishman et al. |
| 8,546,321 B2 | 10/2013 | Bock et al. |
| 8,664,231 B2 | 3/2014 | Will |
| 9,173,952 B2 | 11/2015 | Kelley et al. |
| 2008/0234183 A1 | 9/2008 | Hallbrink et al. |
| 2008/0306075 A1 | 12/2008 | Lee et al. |
| 2011/0300148 A1 | 12/2011 | Bock et al. |
| 2013/0157931 A1 | 6/2013 | Kelley et al. |

FOREIGN PATENT DOCUMENTS

| JP | 2002-521019 A | 7/2002 | |
| KR | 10-2002-0032079 A | 5/2002 | |
| KR | 10-2007-0083862 A | 8/2007 | |
| KR | 10-2007-0100261 A | 10/2007 | |
| KR | 10-2009-0079876 A | 7/2009 | |
| KR | 10-2012-0129121 A | 11/2012 | |
| KR | 10-2016-0064726 A | 6/2016 | |
| WO | 00/64486 A2 | 11/2000 | |
| WO | 03/106491 A2 | 12/2003 | |
| WO | 2006/049442 A1 | 5/2006 | |
| WO | WO-2010054667 A1 * | 5/2010 | ............. A61P 13/08 |
| WO | 2016/085279 A2 | 6/2016 | |

OTHER PUBLICATIONS

Innovagen, Peptide Solubility Calculator for YARVRRRGPRR, accessed on Aug. 27, 2021.*
Innovagen, Peptide Solubility Calculator for RRRRRRRR, accessed on Aug. 27, 2021.*
Ildiko Szabo, European Journal of Medicinal Chemistry 115 (Mar. 2016) 361-368.*
Japanese Office Action for Japanese Patent Application No. 2019-561985 dated Dec. 8, 2020, 6 pages.
Szabo, I. et al., "Cell-penetrating conjugates of pentaglutamylated methotrexate as potential anticancer drugs against resistant tumor cells", European Journal of Medicinal Chemistr, 115: 361-368 (2016).
Extended European Search Report from European Application No. 18798236.8, dated Apr. 23, 2020.
Office Action (First Examination Report) from Indian Application No. 201917047287, dated Feb. 21, 2020.

(Continued)

*Primary Examiner* — Julie Ha
*Assistant Examiner* — Erinne R Dabkowski
(74) *Attorney, Agent, or Firm* — Merchant & Gould P.C.

(57) ABSTRACT

The present invention relates to a compound having a structure in which methotrexate and a peptide are connected via a covalent bond, and an anticancer or anti-inflammatory pharmaceutical composition comprising same. The compound having a structure in which methotrexate and a peptide are connected via a covalent bond of the present invention has excellent biological activity such as anticancer or anti-inflammatory action and has markedly reduced toxicity with respect to cells, and thus, may be usefully used in various fields such as medicine and medical supplies.

4 Claims, 11 Drawing Sheets

Specification includes a Sequence Listing.

(56) References Cited

OTHER PUBLICATIONS

Merrifield, "Solid Phase Peptide Synthesis. I. The Synthesis of a Tetrapeptide", J. Amer. Chem. Soc., 85:2149-54 (1963).

Chau et al., "Synthesis and Characterization of Dextran-Peptide-Methotrexate Conjugates for Tumor Targeting via Mediation by Matrix Metalloproteinase II and Matrix Metalloproteinase IX", Bioconjugate Chemistry, 15, pp. 931-941 (2004).

Chau et al., "Antitumor efficacy of a novel polymer-peptide-drug conjugate in human tumor xenograft models", Int. Journal of Cancer,118, pp. 1519-1526 (2006).

Koczan et al., "Methotrexate Conjugate with Branched Polypeptide Influences Leishmania donovani Infection in Vitro and in Experimental Animals", Bioconjugate Chemistry, 13, pp. 518-524 (2002).

Choi et al., "Comparison of High Dose Methotrexate Administration Between the Inpatient and Outpatient Setting in Children with Acute Lymphoblastic Leukemia", Asian Oncol. Nurs., vol. 14, No. 2, pp. 93-99 (2014).

International Search Report from International Application No. PCT/KR2018/005448 (dated Aug. 14, 2018).

Written Opinion from International Application No. PCT/KR2018/005448 (dated Aug. 14, 2018).

\* cited by examiner

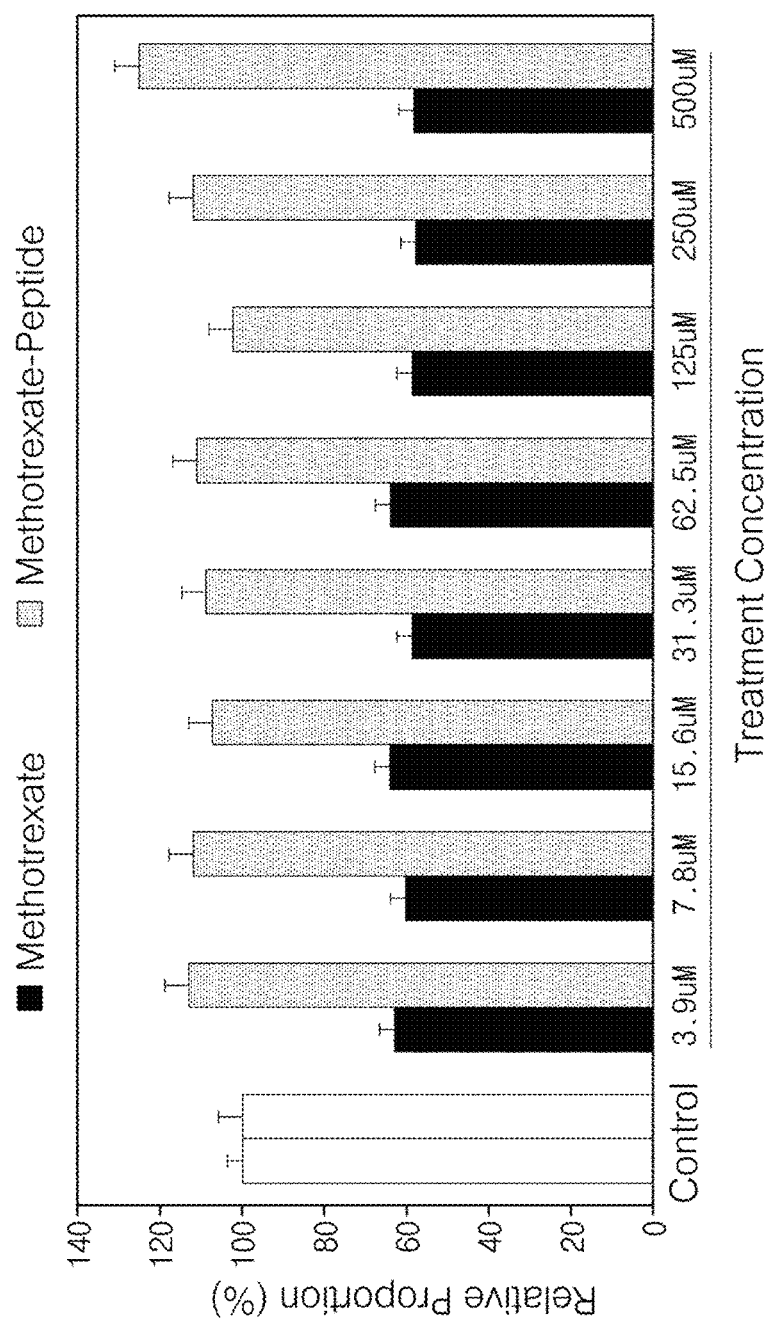
[Fig. 1A]

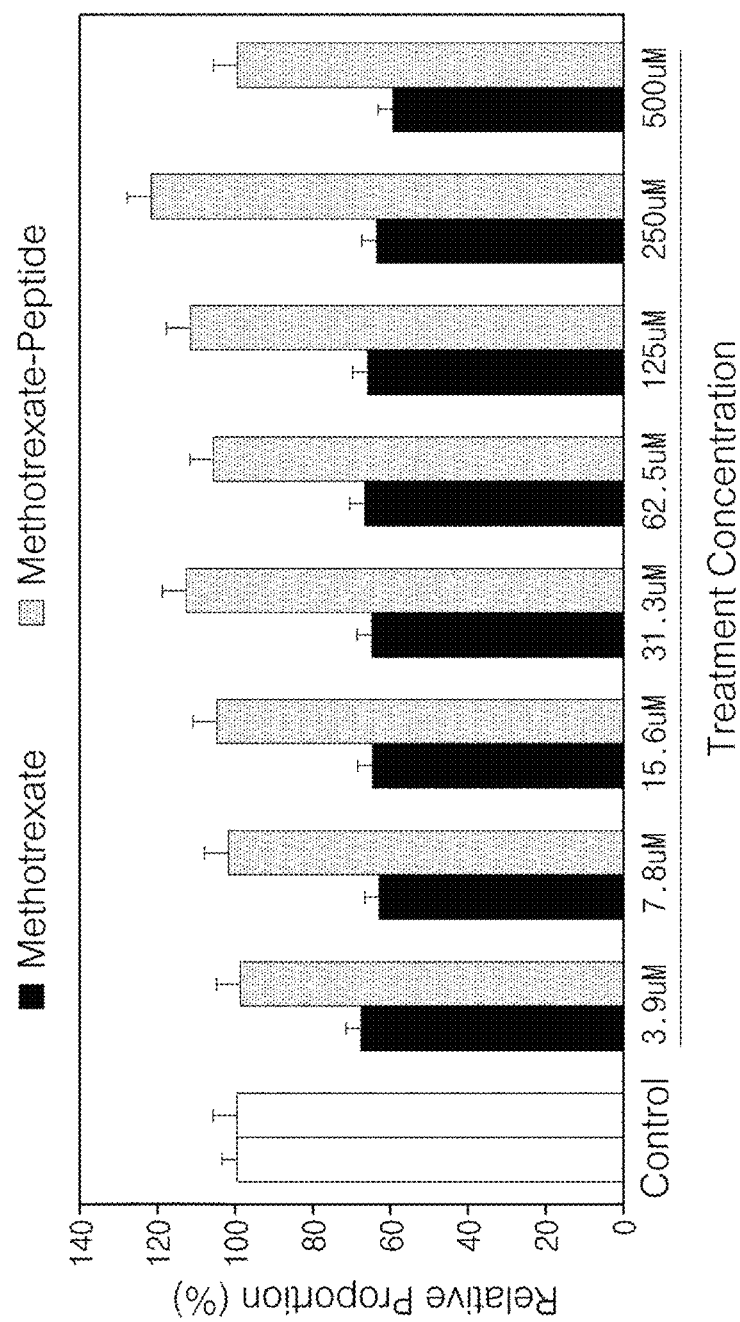
[Fig. 1B]

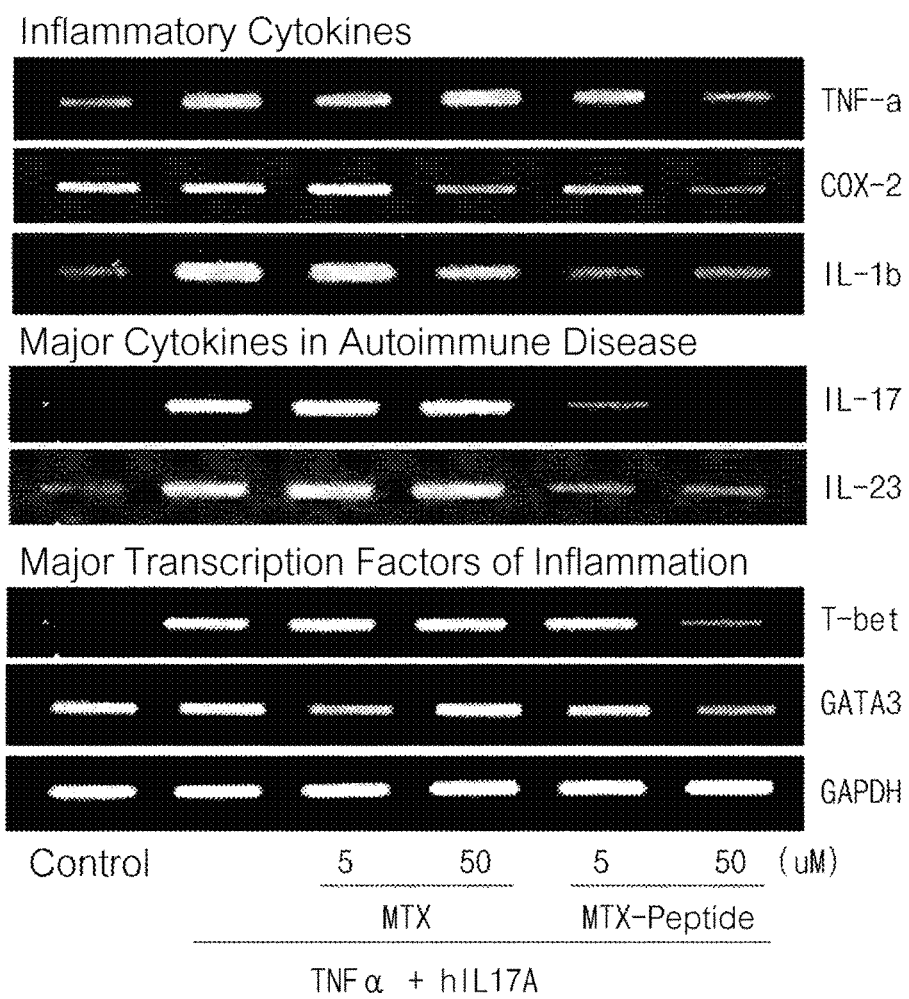
[Fig. 2]

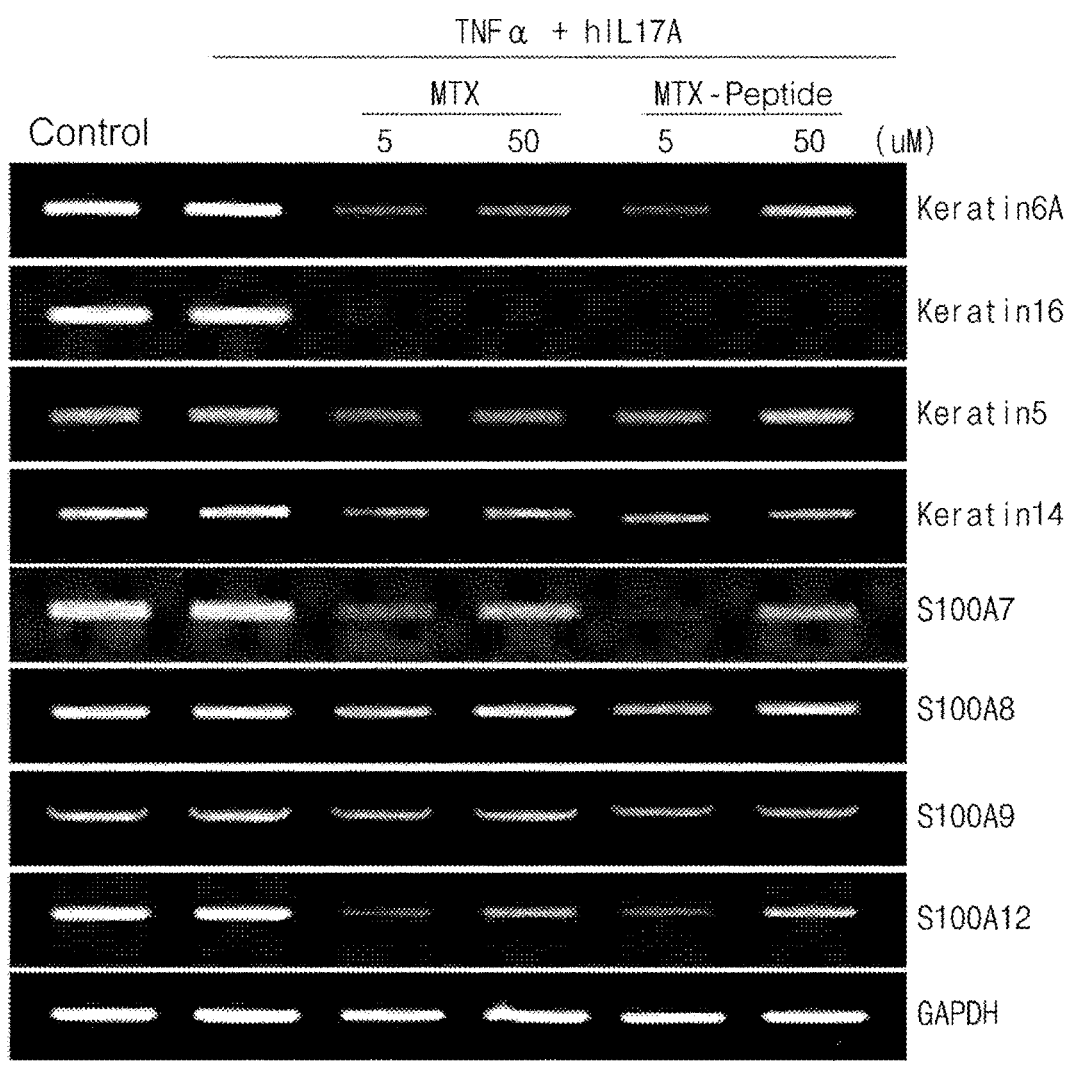
[Fig. 3]

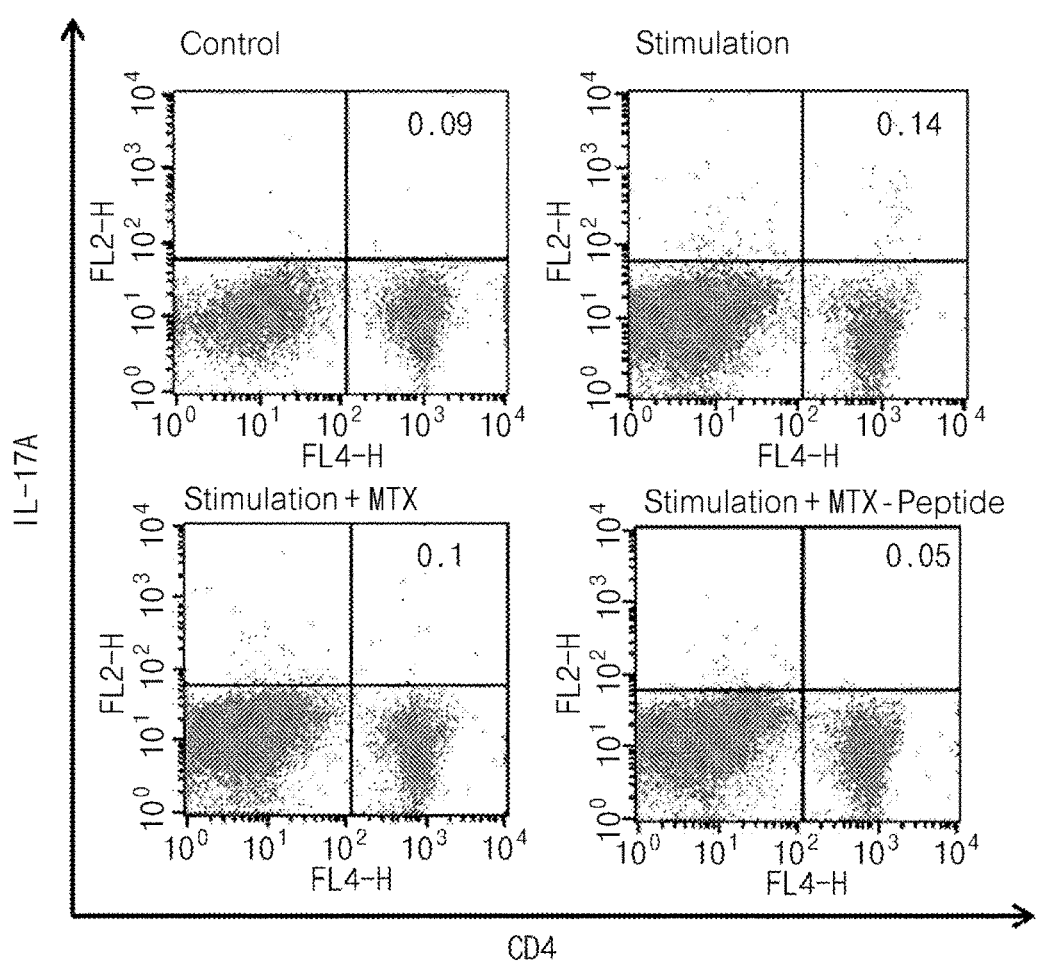
[Fig. 4A]

[Fig. 4B]
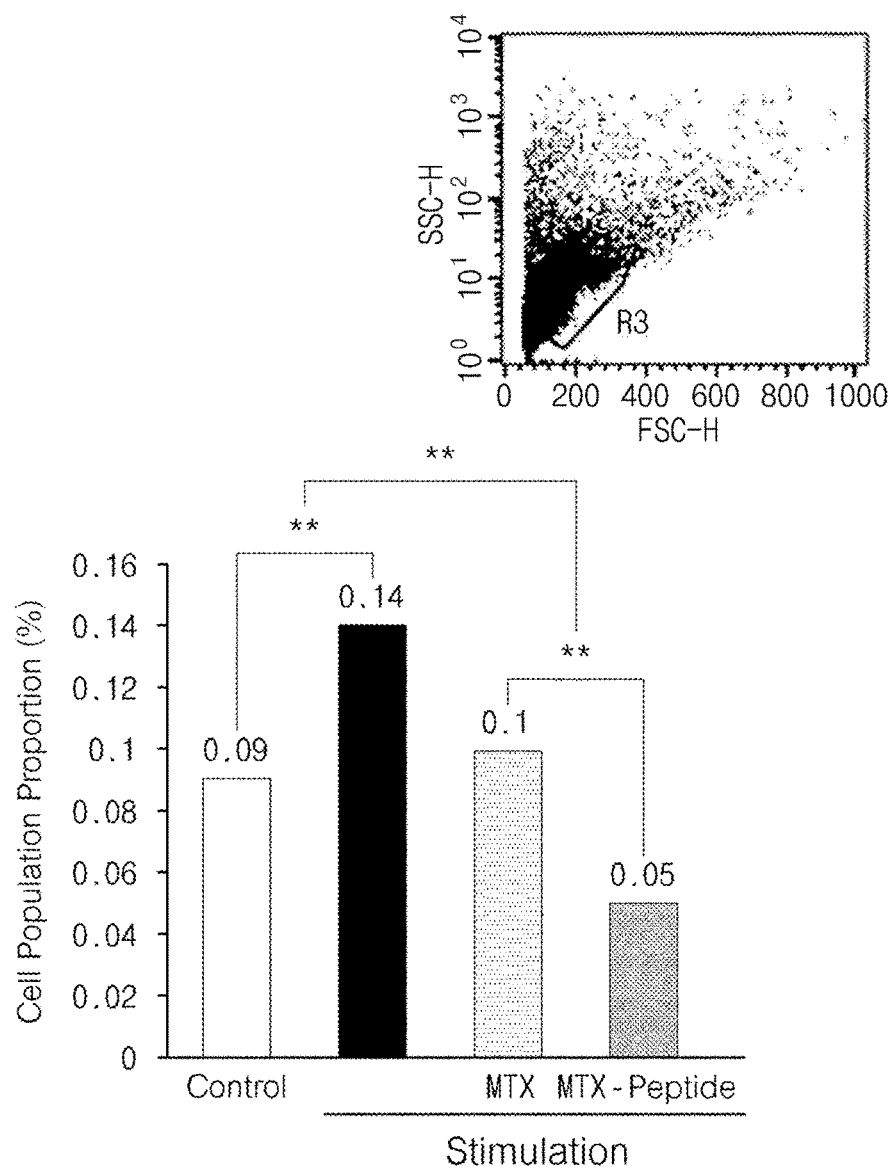

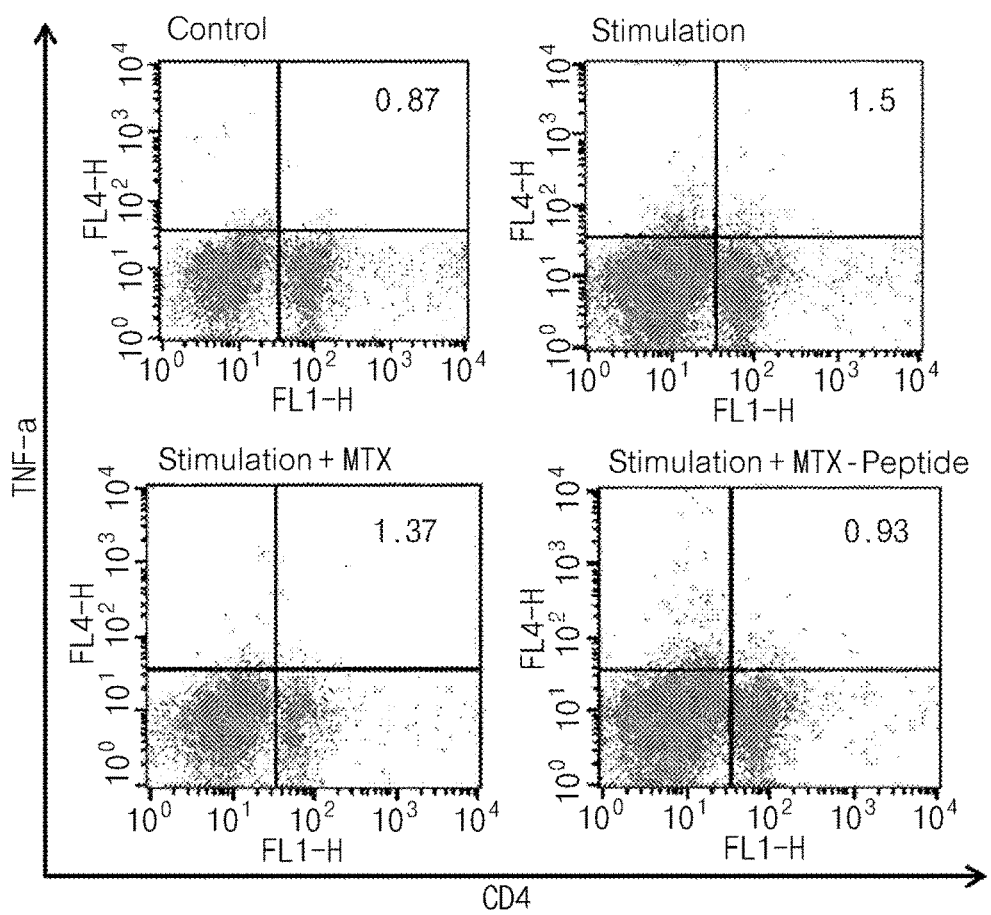
[Fig. 5A]

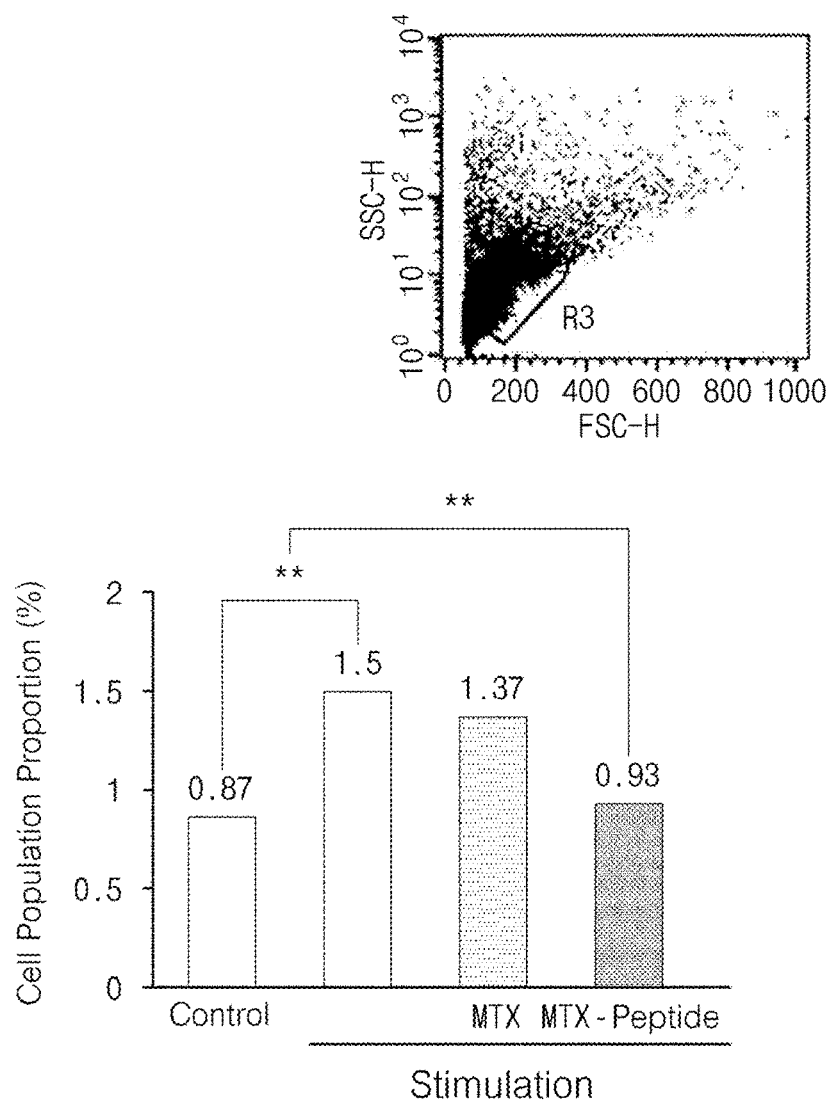
[Fig. 5B]

[Fig. 6]
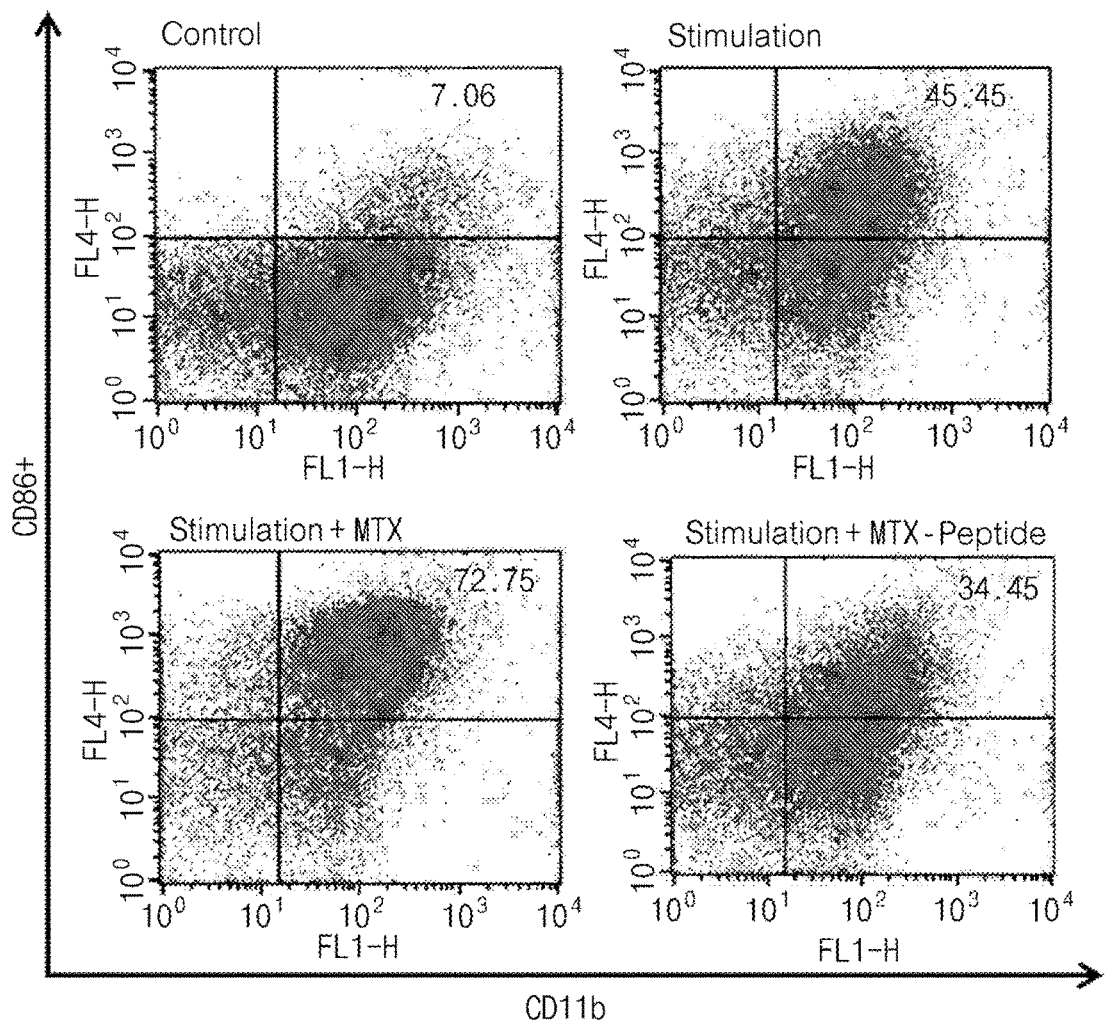

[Fig. 7]

| Secreted Concentration (ng/ml) | | | INF-$\gamma$ | IL-17A |
|---|---|---|---|---|
| Sample ID | | | | |
| Control | | | 1 | 5 |
| Stimulation | | | 1188 | 2913 |
| | MTX | 5uM | 841 | 1901 |
| | | 50uM | 881 | 1417 |
| | MTX - Peptide | 5uM | 759 | 1673 |
| | | 50uM | 827 | 1350 |

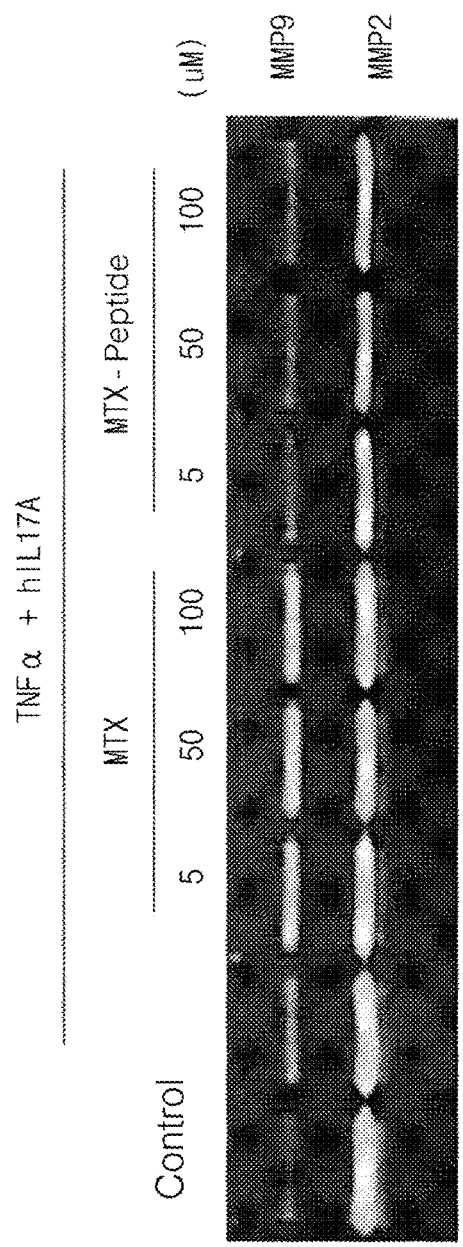
[Fig. 8]

SEQUENCE LISTING

<160> NUMBER OF SEQ ID NOS: 33

<210> SEQ ID NO 1
<211> LENGTH: 11
<212> TYPE: PRT
<213> ORGANISM: Artificial Sequence
<220> FEATURE:
<223> OTHER INFORMATION: Peptide 1

<400> SEQUENCE: 1

Arg Phe Leu Lys Arg Leu Asp Arg Asn Leu Trp
1               5                   10

<210> SEQ ID NO 2
<211> LENGTH: 21
<212> TYPE: DNA
<213> ORGANISM: Artificial Sequence
<220> FEATURE:

<223> OTHER INFORMATION: Forward primer for TNF-alpha

<400> SEQUENCE: 2
aacatccaac cttcccaaac g                                           21

<210> SEQ ID NO 3
<211> LENGTH: 21
<212> TYPE: DNA
<213> ORGANISM: Artificial Sequence
<220> FEATURE:
<223> OTHER INFORMATION: Reverse primer for TNF-alpha

<400> SEQUENCE: 3
gaccctaagc ccccaattct c                                           21

<210> SEQ ID NO 4
<211> LENGTH: 21
<212> TYPE: DNA
<213> ORGANISM: Artificial Sequence
<220> FEATURE:
<223> OTHER INFORMATION: Forward primer for COX-2

<400> SEQUENCE: 4
atcattcacc aggcaaattg c                                           21

<210> SEQ ID NO 5
<211> LENGTH: 21
<212> TYPE: DNA
<213> ORGANISM: Artificial Sequence
<220> FEATURE:
<223> OTHER INFORMATION: Reverse primer for COX-2

<400> SEQUENCE: 5
ggcttcagca taaagcgttt g                                           21

<210> SEQ ID NO 6
<211> LENGTH: 20
<212> TYPE: DNA
<213> ORGANISM: Artificial Sequence
<220> FEATURE:
<223> OTHER INFORMATION: Forward primer for IL-1beta

<400> SEQUENCE: 6
ttcgacacat gggataacga                                             20

<210> SEQ ID NO 7
<211> LENGTH: 20
<212> TYPE: DNA
<213> ORGANISM: Artificial Sequence
<220> FEATURE:
<223> OTHER INFORMATION: Reverse primer for IL-1beta

<400> SEQUENCE: 7
tctttcaaca cgcaggacag                                             20

<210> SEQ ID NO 8
<211> LENGTH: 24
<212> TYPE: DNA
<213> ORGANISM: Artificial Sequence
<220> FEATURE:
<223> OTHER INFORMATION: Forward primer for IL-17

<400> SEQUENCE: 8
ggtcaacctc aaagtcttta actc                                        24

```
<210> SEQ ID NO 9
<211> LENGTH: 24
<212> TYPE: DNA
<213> ORGANISM: Artificial Sequence
<220> FEATURE:
<223> OTHER INFORMATION: Reverse primer for IL-17

<400> SEQUENCE: 9
ttaaaaatgc aagtaagttt gctg                                              24

<210> SEQ ID NO 10
<211> LENGTH: 27
<212> TYPE: DNA
<213> ORGANISM: Artificial Sequence
<220> FEATURE:
<223> OTHER INFORMATION: Forward primer for IL-23

<400> SEQUENCE: 10
agcgggacat atgaatctac taagaga                                           27

<210> SEQ ID NO 11
<211> LENGTH: 25
<212> TYPE: DNA
<213> ORGANISM: Artificial Sequence
<220> FEATURE:
<223> OTHER INFORMATION: Reverse primer for IL-23

<400> SEQUENCE: 11
gtcctagtag ggaggtgtga agttg                                             25

<210> SEQ ID NO 12
<211> LENGTH: 22
<212> TYPE: DNA
<213> ORGANISM: Artificial Sequence
<220> FEATURE:
<223> OTHER INFORMATION: Forward primer for T-bet

<400> SEQUENCE: 12
cctcttctat ccaaccagta tc                                                22

<210> SEQ ID NO 13
<211> LENGTH: 19
<212> TYPE: DNA
<213> ORGANISM: Artificial Sequence
<220> FEATURE:
<223> OTHER INFORMATION: Reverse primer for T-bet

<400> SEQUENCE: 13
ctccgcttca taactgtgt                                                    19

<210> SEQ ID NO 14
<211> LENGTH: 21
<212> TYPE: DNA
<213> ORGANISM: Artificial Sequence
<220> FEATURE:
<223> OTHER INFORMATION: Forward primer for GATA3

<400> SEQUENCE: 14
gaaggcatcc agacccgaaa c                                                 21

<210> SEQ ID NO 15
<211> LENGTH: 20
<212> TYPE: DNA
<213> ORGANISM: Artificial Sequence
<220> FEATURE:
<223> OTHER INFORMATION: Reverse primer for GATA3
```

```
<400> SEQUENCE: 15
acccatggcg gtgaccatgc                                               20

<210> SEQ ID NO 16
<211> LENGTH: 21
<212> TYPE: DNA
<213> ORGANISM: Artificial Sequence
<220> FEATURE:
<223> OTHER INFORMATION: Forward primer for GAPDH

<400> SEQUENCE: 16
gaaggcatcc agacccgaaa c                                             21

<210> SEQ ID NO 17
<211> LENGTH: 20
<212> TYPE: DNA
<213> ORGANISM: Artificial Sequence
<220> FEATURE:
<223> OTHER INFORMATION: Reverse primer for GAPDH

<400> SEQUENCE: 17
acccatggcg gtgaccatgc                                               20

<210> SEQ ID NO 18
<211> LENGTH: 22
<212> TYPE: DNA
<213> ORGANISM: Artificial Sequence
<220> FEATURE:
<223> OTHER INFORMATION: Forward primer for Keratin6A

<400> SEQUENCE: 18
tgcccacctt tcctcccagc aa                                            22

<210> SEQ ID NO 19
<211> LENGTH: 20
<212> TYPE: DNA
<213> ORGANISM: Artificial Sequence
<220> FEATURE:
<223> OTHER INFORMATION: Reverse primer for Keratin6A

<400> SEQUENCE: 19
ccgggtctga cggctcgaag                                               20

<210> SEQ ID NO 20
<211> LENGTH: 21
<212> TYPE: DNA
<213> ORGANISM: Artificial Sequence
<220> FEATURE:
<223> OTHER INFORMATION: Forward primer for Keratin16

<400> SEQUENCE: 20
tggacgtgaa gacgcggctg g                                             21

<210> SEQ ID NO 21
<211> LENGTH: 22
<212> TYPE: DNA
<213> ORGANISM: Artificial Sequence
<220> FEATURE:
<223> OTHER INFORMATION: Reverse primer for Keratin16

<400> SEQUENCE: 21
gatttggcgg ctggaggagg tc                                            22

<210> SEQ ID NO 22
<211> LENGTH: 17
```

```
<212> TYPE: DNA
<213> ORGANISM: Artificial Sequence
<220> FEATURE:
<223> OTHER INFORMATION: Forward primer for Keratin5

<400> SEQUENCE: 22
ctaaagtgcg tctgcta                                                  17

<210> SEQ ID NO 23
<211> LENGTH: 19
<212> TYPE: DNA
<213> ORGANISM: Artificial Sequence
<220> FEATURE:
<223> OTHER INFORMATION: Reverse primer for Keratin5

<400> SEQUENCE: 23
tgggtgctca gatggtata                                                19

<210> SEQ ID NO 24
<211> LENGTH: 21
<212> TYPE: DNA
<213> ORGANISM: Artificial Sequence
<220> FEATURE:
<223> OTHER INFORMATION: Forward primer for Keratin14

<400> SEQUENCE: 24
ctgctggagg gcgaggaatg c                                             21

<210> SEQ ID NO 25
<211> LENGTH: 20
<212> TYPE: DNA
<213> ORGANISM: Artificial Sequence
<220> FEATURE:
<223> OTHER INFORMATION: Reverse primer for Keratin14

<400> SEQUENCE: 25
ccaccgaggc caccgccata                                               20

<210> SEQ ID NO 26
<211> LENGTH: 20
<212> TYPE: DNA
<213> ORGANISM: Artificial Sequence
<220> FEATURE:
<223> OTHER INFORMATION: Forward primer for S100A7

<400> SEQUENCE: 26
aggtccataa taggcatgat                                               20

<210> SEQ ID NO 27
<211> LENGTH: 20
<212> TYPE: DNA
<213> ORGANISM: Artificial Sequence
<220> FEATURE:
<223> OTHER INFORMATION: Reverse primer for S100A7

<400> SEQUENCE: 27
caaggacaga aactcagaaa                                               20

<210> SEQ ID NO 28
<211> LENGTH: 20
<212> TYPE: DNA
<213> ORGANISM: Artificial Sequence
<220> FEATURE:
<223> OTHER INFORMATION: Forward primer for S100A8

<400> SEQUENCE: 28
```

```
atttccatgc cgtctacagg                                              20

<210> SEQ ID NO 29
<211> LENGTH: 20
<212> TYPE: DNA
<213> ORGANISM: Artificial Sequence
<220> FEATURE:
<223> OTHER INFORMATION: Reverse primer for S100A8

<400> SEQUENCE: 29
gcccagtaac tcagctactc                                              20

<210> SEQ ID NO 30
<211> LENGTH: 20
<212> TYPE: DNA
<213> ORGANISM: Artificial Sequence
<220> FEATURE:
<223> OTHER INFORMATION: Forward primer for S100A9

<400> SEQUENCE: 30
gtcgcagctg gaacgcaaca                                              20

<210> SEQ ID NO 31
<211> LENGTH: 20
<212> TYPE: DNA
<213> ORGANISM: Artificial Sequence
<220> FEATURE:
<223> OTHER INFORMATION: Reverse primer for S100A9

<400> SEQUENCE: 31
cctggcctcc tgattagtgg                                              20

<210> SEQ ID NO 32
<211> LENGTH: 20
<212> TYPE: DNA
<213> ORGANISM: Artificial Sequence
<220> FEATURE:
<223> OTHER INFORMATION: Forward primer for S100A12

<400> SEQUENCE: 32
cctctctaag ggtgagctga                                              20

<210> SEQ ID NO 33
<211> LENGTH: 20
<212> TYPE: DNA
<213> ORGANISM: Artificial Sequence
<220> FEATURE:
<223> OTHER INFORMATION: Reverse primer for S100A12

<400> SEQUENCE: 33
ctgggttttg gtgagggaaa                                              20
```

CONJUGATE OF METHOTREXATE AND PEPTIDE

This application is a National Stage Application of PCT/KR2018/005448, filed May 11, 2018, which claims benefit of Serial No. 10-2017-0058867, filed May 11, 2017 in the Republic of Korea and which applications are incorporated herein by reference. To the extent appropriate, a claim of priority is made to each of the above disclosed applications.

TECHNICAL FIELD

The prevent invention relates to a compound having a structure in which methotrexate and a peptide are connected to each other via a covalent bond, and the use thereof.

BACKGROUND ART

Methotrexate (MTX) is the most commonly used drug for the treatment of various childhood cancers, including acute lymphoblastic leukemia, osteosarcoma, and non-Hodgkin's lymphoma, and is used as an important drug in in consolidation and maintenance therapy of acute lymphoblastic leukemia. Methotrexate is an antimetabolite and is a drug that exhibits the anti-proliferative cytotoxic effect by binding to dihydrofolate reductase, an essential enzyme for converting dihydrofolate (FH2) to tetrahydrofolate (FH4) and inhibiting FH4 production, thereby inhibiting DNA, RNA, and protein synthesis. When administered at high doses, 90% of the dose is excreted in the urine, and thus, the excretion of methotrexate is closely related to renal function. Since delayed excretion after the administration of methotrexate increases the likelihood of side effects due to the accumulation of drugs, monitoring the drug concentration after administration is very important. Common side effects that may occur after the administration of methotrexate are hepatotoxicity, nephrotoxicity, hematological toxicity, stomatitis, and neurological symptom, and the like, and mortality from toxicity was reported to be about 5-6%. Methotrexate is present in cells in combination with polyglutamic acid such as folic acid.

In addition, methotrexate is known to be useful in the treatment of inflammatory diseases. In this regard, Korea Patent Laying-Open No. 2009-0079876 discloses the use of methotrexate solution for the treatment of inflammatory autoimmune diseases; Korea Patent Laying-Open No. 2007-0100261 discloses a method of treating inflammation, comprising administering a combination of an effective amount of methotrexate and an A3 adenosine receptor agonist (A3AR agonist); Korea Patent Laying-Open No. 2007-0083862 discloses a transdermal pharmaceutical composition for the treatment of autoimmune disease, comprising a conjugate of methotrexate and protein transduction domain (PTD), and an excipient; and Korea Patent Laying-Open No. 2002-0032079 discloses a composition for transdermal administration for the treatment of arthritis, containing methotrexate as an effective component.

However, it is known that the use of such methotrexate may cause side effects such as bone marrow destruction, plaque destruction due to excessive bleeding, bleeding in the digestive organs, gastrointestinal perforation, hair loss, impairment of liver and kidney function, and the like.

Therefore, there is a need for the development of novel compounds that can reduce the side effects of methotrexate having characteristics as described above, and further enhance the physiological efficacy.

DISCLOSURE

Technical Problem

The present invention is to improve the problems of the conventional methotrexate as described above, and it is a technical object of the present invention to provide a novel methotrexate-derived compound which exhibits identical or better physiological activity compared to the natural methotrexate and has reduced side effects.

Technical Solution

In order to achieve the above object, the present invention provides a compound having a structure in which methotrexate and a peptide are connected to each other via a covalent bond.

According to an embodiment of the present invention, the peptide may consist of the sequence of 2 to 30, preferably 5 to 20, more preferably 8 to 15, more preferably 10 to 12 amino acids, but is not limited thereto.

According to another embodiment of the present invention, the peptide is preferably, but not limited to, a water-soluble peptide. According to a preferred embodiment of the present invention, it is preferred that the proportion of amino acids having a hydrophilic side chain in the water-soluble peptide is as high as 50% or more, preferably 60% or more, more preferably 70% or more, more preferably 80% or more, more preferably 90% or more, and most preferably 100%. According to another preferred embodiment of the present invention, the amino acid having a hydrophobic side chain in the water-soluble peptide is present in 5 or less, preferably 4 or less, more preferably 3 or less, more preferably 2 or less, more preferably 1 or less, and most preferably none.

According to another embodiment of the present invention, the peptide may be a peptide consisting of the amino acid sequence of SEQ ID NO: 1, but is not limited thereto. Further, the present invention provides an anti-cancer or anti-inflammatory pharmaceutical composition comprising any one of the compounds as described above.

According to an embodiment of the present invention, the pharmaceutical composition may be formulated and used in the form of oral formulations such as powders, granules, tablets, capsules, suspensions, emulsions, and syrups, external preparations, suppositories, and sterile injectable solutions, but is not limited thereto.

Advantageous Effects

The compound having a structure in which methotrexate and a peptide are connected via a covalent bond of the present invention has excellent physiological activity such as anti-cancer or anti-inflammatory action and has markedly reduced toxicity with respect to cells, and thus, may be usefully used in various fields such as medicines and medical supplies.

DESCRIPTION OF DRAWINGS

FIGS. 1A and 1B are graphs showing the effects of the compounds according to the present invention and methotrexate on cell proliferation in fibroblasts and keratinocytes.

FIGS. 2 and 3 are RT-PCR electrophoresis photographs showing the effects of the compounds according to the present invention and methotrexate on the expression of genes associated with inflammation in splenocytes and keratinocytes.

FIGS. 4A and 4B are flow cytometry (FACS) graphs showing the effects of the compounds according to the present invention and methotrexate on IL-17-positive cell population in splenocytes.

FIGS. 5A and 5B are flow cytometry (FACS) graphs showing the effects of the compounds according to the present invention and methotrexate on TNF-α-positive cell population in macrophage lines.

FIG. 6 is a flow cytometry (FACS) graph showing the effects of the compounds according to the present invention and methotrexate on activated immune and APC-positive cell populations in splenocytes.

FIG. 7 is a graph showing the effects of the compounds according to the present invention and methotrexate on the expression of inflammatory cytokines in splenocytes.

FIG. 8 is an electrophoretic photograph and a graph showing the effects of the compounds according to the present invention and methotrexate on the activity of matrix metalloproteinase (MMP) in keratinocyte lines.

BEST MODE

In order to achieve the above object, the present invention provides a compound having a structure in which methotrexate and a peptide are connected to each other via a covalent bond.

The methotrexate represents a compound of the formula $C_2OH_{22}N_8O_5$ having a chemical structure represented by the following chemical formula:

[Chemical Formula]

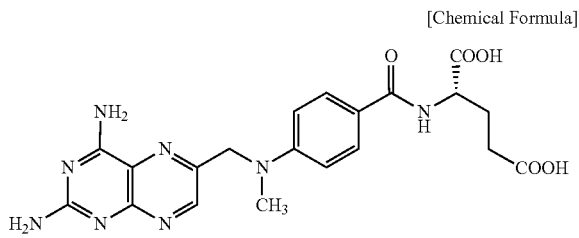 [SMILES: CN(Cc1cnc2nc(N)nc(N)c2n1)c1ccc(C(=O)N[C@@H](CCC(=O)O)C(=O)O)cc1]

As used herein, the term "peptide" refers to a linear molecule which is formed by linking amino acids to each other via a peptide bond. The peptides may be prepared according to conventional biological or chemical synthesis methods known in the art, in particular solid-phase synthesis techniques (Merrifield, *J. Amer. Chem. Soc.*, 85:2149-54 (1963); Stewart et al., Solid Phase Peptide Synthesis, 2nd ed., Pierce Chem. Co. Rockford, 111(1984)).

The peptide is preferably, but is not limited to, a water-soluble peptide. According to an embodiment of the present invention, the peptide consists of 2 to 30, preferably 5 to 20, more preferably 8 to 15, more preferably 10 to 12 amino acids. According to a preferred embodiment of the present invention, it is preferred that the proportion of amino acids having a hydrophilic side chain in the peptide is as high as 50% or more, preferably 60% or more, more preferably 70% or more, more preferably 80% or more, more preferably 90% or more, and most preferably 100%. On the other hand, it is preferred that the proportion of amino acids having a hydrophobic side chain in the peptide is as low as less than 50%, preferably 40% or less, more preferably 30% or less, more preferably 20% or less, more preferably 10% or less, and most preferably 0%. As used herein, the term "amino acids having a hydrophilic side chain" represents, but is not limited to, arginine (Arg), histidine (His), lysine (Lys), aspartic acid (Asp), glutamic acid (Glu), serine (Ser), threonine (Thr), asparagine (Asn), glutamine (Gln), cysteine (Cys), selenocysteine (Sec), glycine (Gly), and proline (Pro); the term "amino acids having a hydrophobic side chain" represents, but is not limited to, alanine (Ala), valine (Val), isoleucine (Ile), leucine (Leu), methionine (Met), phenylalanine (Phe), tyrosine (Tyr), and tryptophan (Trp); and, in addition to amino acids present in nature as described above, modifications thereof may be used without limitation. According to a preferred embodiment of the present invention, the amino acids having the hydrophobic side chain in the peptide are present in 5 or less, preferably 4 or less, more preferably 3 or less, more preferably 2 or less, more preferably 1 or less, and most preferably none. According to an embodiment of the present invention, the peptide is preferably, but is not limited to, a peptide consisting of the amino acid sequences of SEQ ID NOs: 1 to 4.

According to an embodiment of the present invention, the compounds of the present invention exhibit remarkably lower cytotoxicity compared to methotrexate used as a positive control group (see FIG. 1) and can also remarkably reduce the expression of genes associated with intracellular inflammatory responses (see FIGS. 2 and 3). According to another embodiment of the present invention, the compounds of the present invention can remarkably reduce the number of IL-17, TNF-α, activated immune, and APC-positive cell populations (see FIGS. 4 to 6). According to another embodiment of the present invention, the compounds of the present invention not only can remarkably reduce the secretion of the inflammatory cytokines IFN-γ and IL-17A (see FIG. 7), but also remarkably reduce the expression of the MMP gene (see FIG. 8).

The compound of the present invention has excellent stability in itself, but may further improve stability by modifying any amino acid constituting the peptide bound to the compound. According to an embodiment of the invention, the N-terminus of the peptide may be combined with the protecting group selected from the group consisting of acetyl group, fluorenyl methoxy carbonyl group, formyl group, palmitoyl group, myristyl group, stearyl group, and polyethylene glycol (PEG) to further improve stability. According to another embodiment of the invention, the peptide may be combined with the protecting group selected from the group consisting of acetyl group, fluorenyl methoxy carbonyl group, formyl group, palmitoyl group, myristyl group, stearyl group, and polyethylene glycol (PEG) to further improve stability.

Modifications of amino acids as described above act to greatly improve the stability of the compounds of the present invention. As used herein, the term "stability" is used as a meaning encompassing not only "in vivo" stability but also "in vitro" stability such as storage stability (for example, room temperature storage stability). In addition, the above-mentioned protecting group acts to protect the compounds of the present invention against the attack of a protein cleaving enzyme in vivo and in vitro.

In addition, the present invention provides an ant-cancer or anti-inflammatory composition comprising the compound as an active ingredient. In the present invention, the composition may be in the form of a pharmaceutical composition, but is not limited thereto.

Since the composition of the present invention comprises the compound of the present invention as described above as an active ingredient, the common content between the both is omitted in order to avoid excessive complexity of the present specification.

According to a preferred embodiment of the present invention, the composition of the present invention is a pharmaceutical composition comprising: (a) a pharmaceutically effective amount of the compound of the present invention as described above; and (b) a pharmaceutically acceptable carrier.

As used herein, the term "a pharmaceutically effective amount" means an amount sufficient to achieve the efficacy or activity of the compound of the invention as described above.

In an embodiment of the present invention, the cancer is used as a meaning including, without limitation, hematologic malignancies such as acute lymphoblastic leukemia, osteosarcoma, and non-Hodgkin's lymphoma, as well as solid cancers such as gastric cancer, liver cancer, lung cancer, colorectal cancer, prostate cancer, malignant melanoma, breast cancer, and uterine cancer. In addition, in another embodiment of the present invention, the pharmaceutical composition of the present invention may be used for the prevention or treatment of autoimmune diseases associated with an inflammatory response. The autoimmune diseases associated with the inflammatory response include, but are not limited to, rheumatoid arthritis, Behcet's disease, Crohn's disease, rhinitis, asthma, and the like.

The pharmaceutically acceptable carriers comprised in the pharmaceutical composition of the present invention are those conventionally used in the formulation and include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil. The pharmaceutical composition of the present invention may further comprise a lubricant, a wetting agent, a sweetener, a flavoring agent, an emulsifier, a suspending agent, a preservative, and the like, in addition to the ingredients as described above. Suitable pharmaceutically acceptable carriers and agents are described in detail in Remington's Pharmaceutical Sciences (19th ed., 1995).

The pharmaceutical composition of the present invention may be prepared in a unit-dose form by formulating the compound of the present invention with a pharmaceutically acceptable carrier and/or excipient according to methods which may be easily carried out by those skilled in the art, or prepared by incorporating it into a multi-dose container. Wherein, the formulation may be in the form of a solution, suspension, or emulsion in an oil or aqueous medium, or in the form of an extract, a powder, a granule, a tablet, a capsule, or a gel (for example, a hydrogel), and may further comprise a dispersing agent and/or a stabilizer.

The pharmaceutical composition according to the present invention may be administered orally or parenterally in clinical administration and used in the form of general pharmaceutical formulation. That is, the pharmaceutical composition of the present invention may be administered in a variety of oral and parenteral formulations in actual clinical administration, and are prepared using diluents or excipients, such as a filler, an extender, a binder, a wetting agent, a disintegrating agent, and a surfactant, which are usually used when formulated. Solid formulations for oral administration include a tablet, a pill, a powder, a granule, a capsule, and the like, and such solid formulations are prepared by mixing at least one excipient such as starch, calcium carbonate, sucrose or lactose, and gelatin with the herbal extract or herbal fermentation product. In addition to simple excipients, lubricants such as magnesium stearate and talc are also used. Liquid formulations for oral administration include a suspension, a solution for internal use, an emulsion, and a syrup, and the like, and may include various excipients, such as a wetting agent, a sweetener, a flavoring agent, a preservative, and the like, in addition to commonly used simple diluents such as water and liquid paraffin. Formulations for parenteral administration include a sterile aqueous solution, a non-aqueous solution, a suspension, an emulsion, a lyophilized formulation, and a suppository. As the non-aqueous solvent and the suspension solvent, propylene glycol, polyethylene glycol, vegetable oils such as olive oil, injectable esters such as ethyl oleate, and the like may be used. As the base of the suppository, witepsol, macrogol, tween 61, cacao butter, laurin, glycerol, gelatin, and the like may be used.

The dosage unit may contain, for example, 1, 2, 3 or 4 times, or ½, ⅓ or ¼ times the individual dosage. Individual dosages contain an amount in which an active drug is administered at one time, and usually correspond to all, ½, ⅓ or ¼ times the daily dose.

The pharmaceutical composition of the present invention may be prepared in a unit-dose form by formulating the compound of the present invention with a pharmaceutically acceptable carrier and/or excipient according to methods which may be easily carried out by those skilled in the art, or prepared by incorporating it into a multi-dose container. Wherein, the formulation may be in the form of a solution, suspension, or emulsion in an oil or aqueous medium, or in the form of an extract, a powder, a granule, a tablet, a capsule, or a gel (for example, a hydrogel), and may further comprise a dispersing agent and/or a stabilizer.

EXAMPLES

Hereinafter, the present invention will be described in detail through examples.

However, the following examples are only for illustrating the present invention, and the content of the present invention is not limited to the following examples.

Example 1. Synthesis of Compounds of Present Invention

<1-1> Synthesis of Peptides of SEQ ID NO: 1

700 mg of chlorotrityl chloride resin (CTL resin; Nova biochem [0064] Cat No. 01-64-0021) was placed in a reaction vessel, and then 10 ml of methylene chloride (MC) was added thereto and stirred for 3 minutes. After removal of the solution, 10 ml of dimethylformamide (DMF) was added thereto and stirred for 3 minutes, and then the solvent was removed again. 10 ml of a dichloromethane solution was placed in the reactor, and subsequently 200 mmol Fmoc-Trp-OH (Bachem, Swiss) and 400 mmol diisopropylethylamine (DIEA) were placed therein and stirred to be well dissolved, and then reaction was carried out with stirring for 1 hour. After completion of the reaction, washing was performed, and methanol and DIEA (2:1) were dissolved in dichloromethane (DCM) and reacted for 10 minutes, and then washing was performed with an excess of DCM/DMF (1:1). Thereafter, the solution was removed, 10 ml of dimethylformamide (DMF) was placed therein and stirred for 3 minutes, and then the solvent was removed again. 10 ml of a deprotecting solution (20% piperidine/DMF) was placed in the reaction vessel and stirred at room temperature for 10 minutes, and then the solution was removed. Thereafter, the same amount of deprotecting solution was placed therein to maintain the reaction for 10 minutes again, and then the solution was removed, and washing was performed twice with DMF, once with MC, and once with DMF for 3 minutes, respectively, to prepare Trp-CTL resins.

10 ml of a DMF solution was placed in a new reactor, and 200 mmol Fmoc-Leu-OH (Bachem, Swiss), 200 mmol HoBt, and 200 mmol Bop were placed therein, and then well dissolved by stirring. 400 mmol DIEA was placed in the reactor twice in fractions and stirred for at least 5 minutes until all solids dissolved. The dissolved amino acid mixture solution was placed in the reaction vessel containing the deprotected resins, and reacted with stirring at room temperature for 1 hour. The reaction solution was removed and stirred three times for each 5 minutes with a DMF solution, and then removed. A small amount of the reacted resin was taken and the degree of reaction was checked using a Kaiser test (Ninhydrin Test). The deprotection reaction was performed twice as described above with the deprotecting solution to prepare a Leu-Trp-CTL resin. The resin was sufficiently washed with DMF and MC, and subjected to the Kaiser test once again to perform an amino acid attachment experiment below in the same manner as described above.

Based on selected amino acid sequences, chain reaction was performed in order of Fmoc-Asn(Trt), Fmoc-Arg(Pbf), Fmoc-Asp(tBu), Fmoc-Leu, Fmoc-Arg(Pbf), Fmoc-Lys(Boc), Fmoc-Leu, Fmoc-Phe, and Fmoc-Arg(Pbf). The Fmoc-protecting group was reacted with a deprotecting solution twice for 10 minutes, and then washed well and removed. The prepared peptidyl resin was washed three times with DMF, MC, and methanol, respectively, and dried by slowly flowing nitrogen air, and then completely dried under reduced pressure vacuum over $P_2O_5$, 30 ml of a leaving solution (95% of trifluoroacetic acid, 2.5% of distilled water, and 2.5% of thioanisole) was placed therein, and the reaction was maintained for 2 hours while shaking at room temperature occasionally. The resin was filtered by filtration and washed with a small volume of TFA solution, and then was combined with the mother liquor. The distillation was carried out using a reduced pressure so that the total volume is remained to be half, and 50 ml of cold ether was added thereto to induce precipitation, which centrifuged to collect the precipitate and washed twice more with cold ether. After removing the mother liquor and sufficiently drying under a nitrogen atmosphere, 1.40 g of the pre-purified peptide RFLKRLDRNLW (SEQ ID NO: 1) was synthesized (yield: 92.4%). The molecular weight of 1516.7 (theoretical value: 1516.8) was obtained when measured using the molecular weight measuring instrument.

TABLE 1

| SEQ ID NO | Amino Acid Sequence | Analytical Value (Mass Spectrometer) | |
|---|---|---|---|
| | | Analytical Value | Theoretical Value |
| 1 | RFLKRLDRNLW | 1516.7 | 1516.8 |

<1-2> Synthesis of Compounds of Present Invention

Peptidyl resin (1 mmol) and 10 ml of 1-methyl-2-pyrrolidone (NMP) were placed in a peptide reactor, and then 270 mg (2.0 equivalents) of 1-hydroxybenzotriazole (HOBt), 759 mg (2.0 equivalents) of N,N,N',N'-tetramethyl-O-(1H-benzotriazol-1-yl)uronium hexafluorophosphate, O-(benzotriazol-1-yl)-N,N,N',N'-tetramethyluronium hexafluorophosphate, and 277 mg (2.0 equivalents) of methotrexate were added thereto and reacted for 30 minutes. 388 mg (3 equivalents) of N,N-diisopropylethylamine (DIEA) was added thereto and reacted at room temperature for 12 to 48 hours, and then filtered to obtain the reacted peptidyl resin. The obtained resin was reacted for 2 hours at room temperature using a cleavage solution, and then the resin and the protecting group were removed and recrystallization was performed using 10 ml (10 mmol) of diethyl ether to obtain a hybrid peptide.

Experimental Example 1. Cytotoxicity Test of Compounds of Present Invention

Cell proliferation experiments were performed to confirm the effect of the methotrexate-peptide compound of the present invention synthesized in Example <1-2> on cytotoxicity. Specifically, NIH3T3 fibroblast lines and HaCaT keratinocyte lines were inoculated into 96-well plates at $1 \times 10^6$ cells/well and cultured, and then the next day, treated with the methotrexate-peptide compound prepared in Example <1-2> above and methotrexate at a concentration of 3.9 to 500 μM, respectively. After culture for 48 hours, the effect of the compounds on cell proliferation was confirmed through MTT analysis using a Ez-cytox kit (Daeillab/Domestic).

As a result, it was confirmed that methotrexate used as a positive control group exhibited a significant degree of cytotoxicity by inhibiting cell proliferation in both cell lines, but the compound having a structure in which methotrexate and a peptide are connected to each other via covalent bond according to the present invention did not exhibit cytotoxicity by showing similar or rather superior cell proliferation activity compared to a non-treated negative control group (FIGS. 1A and 1B).

Experimental Example 2. Inhibitory Effect of Compounds of Present Invention on Inflammation (1)

RT-PCR analysis was performed to confirm the effect of the methotrexate-peptide compound of the present invention synthesized in Example <1-2> on inflammatory responses. Specifically, 6-7 week old mice were sacrificed to obtain spleens, and the spleens were crushed using a cell filter and centrifuged together with serum-free RPMI-1640 medium. The supernatant was discarded and red blood cell (RBC) lysis buffer was used twice to remove RBCs. Thereafter, washing was performed with serum-free RPMI-1640 medium and an appropriate amount of serum-free RPMI-1640 medium was added thereto. Cell number was measured and the cells were inoculated into 24-well plates ($1 \times 10^7$ cells/dish), and then the next day, treated with the methotrexate-peptide compound of the present invention synthesized in Example <1-2> or methotrexate (5 μM and 50 μM), and LPS (10 nM) and IL-17 (200 ng/ml) used as a stimulant.

After culture for 24 hours, RNA extraction kit (Qiagen RNeasy kit) was used to extract the total RNA, and then 3 μg of RNA, 2 μg of random hexamer, and DEPC-treated water were added thereto and reacted at 65° C. for 5 minutes to synthesize single-stranded DNA from RNA. 5× first-strand buffer, 0.1 M DTT, 10 mM dNTP, and reverse transcriptase were placed therein to make a total of 20 ml, and reacted at 42° C. for 1 hour. After heating at 95° C. for 5 minutes again, 20 ml of distilled water was added thereto to make a final 40 ml of cDNA. Polymerase chain reaction (PCR) was performed by mixing 10 pmol primer, 10× Tag buffer, 10 mM dNTP, and i-Tag DNA polymerase as shown in Table 2 below, specific for each of 3 μl of cDNA, TNF-α, COX-2, IL-1β, IL-17, IL-23, T-bet, GATA3, and GAPDH genes. PCR reaction condition was 30 seconds at 94° C., 30 seconds at 55-56° C., and 30 seconds at 72° C. Cycle number genes were analyzed under conditions in which PCR results could be exponentially amplified. 5 ml of the obtained PCR product was electrophoresed on 1% agarose gel and stained with ethidium bromide to confirm the mRNA levels of TNF-α, COX-2, IL-1β, IL-17, IL-23, T-bet, and GATA3 genes associated with inflammation and autoimmune diseases.

TABLE 2

| Factor | | Primer Sequence | SEQ ID NO |
|---|---|---|---|
| TNF-α | Forward (5') | AACATCCAACCTTCCCAAACG (3') | 2 |
| | Reverse (5') | GACCCTAAGCCCCCAATTCTC (3') | 3 |
| COX-2 | Forward (5') | ATCATTCACCAGGCAAATTGC (3') | 4 |
| | Reverse (5') | GGCTTCAGCATAAAGCGTTTG (3') | 5 |
| IL-1β | Forward (5') | TTCGACACATGGGATAACGA (3') | 6 |
| | Reverse (5') | TCTTTCAACACGCAGGACAG (3') | 7 |
| IL-17 | Forward (5') | GGTCAACCTCAAAGTCTTTAACTC (3') | 8 |
| | Reverse (5') | TTAAAAATGCAAGTAAGTTTGCTG (3') | 9 |
| IL-23 | Forward (5') | AGCGGGACATATGAATCTACTAAGAGA (3') | 10 |
| | Reverse (5') | GTCCTAGTAGGGAGGTGTGAAGTTG (3') | 11 |
| T-bet | Forward (5') | CCTCTTCTATCCAACCAGTATC (3') | 12 |
| | Reverse (5') | CTCCGCTTCATAACTGTGT (3') | 13 |
| GATA3 | Forward (5') | GAAGGCATCCAGACCCGAAAC (3') | 14 |
| | Reverse (5') | ACCCATGGCGGTGACCATGC (3') | 15 |
| GAPDH | Forward (5') | GAAGGCATCCAGACCCGAAAC (3') | 16 |
| | Reverse (5') | ACCCATGGCGGTGACCATGC (3') | 17 |

As a result, it was confirmed that the compound having a structure in which methotrexate and a peptide are connected to each other via covalent bond according to the present invention could more remarkably reduce the expression of genes associated with inflammation formation even at a much lower concentration, compared to methotrexate (FIG. 2).

Experimental Example 3. Inhibitory Effect of Compounds of Present Invention on Inflammation (2)

RT-PCR analysis was performed to confirm the effect of the methotrexate-peptide compound of the present invention synthesized in Example <1-2> on inflammatory responses. To this end, RT-PCR was performed in the same manner as in Experimental Example 2 above, except that HaCaT keratinocyte line was used as the cell line, and Keratin6A, Keratin16, Keratin5, Keratin14, S100A7, S100A8, S100A9, and S100A12 related to the progression of psoriasis were used as inflammation-related genes, wherein primers as shown in Table 3 below were used as primers specific for the genes.

TABLE 3

| Factor | | | Primer Sequence | SEQ ID NO |
|---|---|---|---|---|
| Keratin6A | Forward | (5') | TGCCCACCTTTCCTCCCAGCAA (3') | 18 |
| | Reverse | (5') | CCGGGTCTGACGGCTCGAAG (3') | 19 |
| Keratin16 | Forward | (5') | TGGACGTGAAGACGCGGCTGG (3') | 20 |
| | Reverse | (5') | GATTTGGCGGCTGGAGGAGGTC (3') | 21 |
| Keratin5 | Forward | (5') | CTAAAGTGCGTCTGCTA (3') | 22 |
| | Reverse | (5') | TGGGTGCTCAGATGGTATA (3') | 23 |
| Keratin14 | Forward | (5') | CTGCTGGAGGGCGAGGAATGC (3') | 24 |
| | Reverse | (5') | CCACCGAGGCCACCGCCATA (3') | 25 |
| S100A7 | Forward | (5') | AGGTCCATAATAGGCATGAT (3') | 26 |
| | Reverse | (5') | CAAGGACAGAAACTCAGAAA (3') | 27 |
| S100A8 | Forward | (5') | ATTTCCATGCCGTCTACAGG (3') | 28 |
| | Reverse | (5') | GCCCAGTAACTCAGCTACTC (3') | 29 |
| S100A9 | Forward | (5') | GTCGCAGCTGGAACGCAACA (3') | 30 |
| | Reverse | (5') | CCTGGCCTCCTGATTAGTGG (3') | 31 |
| S100A12 | Forward | (5') | CCTCTCTAAGGGTGAGCTGA (3') | 32 |
| | Reverse | (5') | CTGGGTTTTGGTGAGGGAAA (3') | 33 |

As a result, it was confirmed that the compound having a structure in which methotrexate and a peptide are connected to each other via covalent bond according to the present invention not only could significantly reduce toxicity compared to methotrexate, but also remarkably reduce the expression of genes associated with the progression of psoriasis even at a much lower concentration, thus increasing the effect rather than methotrexate (FIG. 3).

Experimental Example 4. Effect of Compounds of Present Invention on IL-17A$^+$/CD4$^+$ Cell Populations A flow cytometry (FACS) was performed to confirm the effect of the methotrexate-peptide compound of the present invention synthesized in Example <1-2> on IL-17A$^+$/CD4$^+$ cell populations. Specifically, splenocytes were isolated from 6-7 week old mice as described in Experimental Example 2 above, and then were treated with the methotrexate-peptide compound of the present invention synthesized in Example <1-2> or methotrexate, LPS (2 ρg/mL) used as the stimulant, and the Th17 differentiation-promoting cytokines TGF-α and IL-23 (20 ng/mL respectively). After 24 hours, the cells were treated with antibodies specific for the Th17 differentiation markers IL-17A and CD4 for 30 minutes, and then washed twice with PBS and FACS analysis was performed.

As a result, it was confirmed that the compound having a structure in which methotrexate and a peptide are connected to each other via covalent bond according to the present invention could remarkably reduce the number of IL-17$^+$/CD4$^+$ cell populations, compared to methotrexate (FIGS. 4A and 4B).

Experimental Example 5. Effect of Compounds of Present Invention on TNF-α$^+$/CD4$^+$ Cell Populations A flow cytometry (FACS) was performed to confirm the effect of the methotrexate-peptide compound of the present invention synthesized in Example <1-2> on TNF-α$^+$/CD4$^+$ cell populations. Specifically, mast cells (Raw264.7) were cultured, and then were treated with the methotrexate-peptide compound of the present invention synthesized in Example <1-2> or methotrexate and LPS used as the stimulant (2 μg/ml). After 24 hours, the cells were treated with antibodies specific for the mast cell activation markers TNF-α and CD4 for 30 minutes, and then washed twice with PBS and FACS analysis was performed.

As a result, it was confirmed that the compound having a structure in which methotrexate and a peptide are connected to each other via covalent bond according to the present invention could remarkably reduce the number of TNF-α$^+$/CD4$^+$ cell populations, compared to methotrexate (FIGS. 5A and 5B).

Experimental Example 6. Effect of Compounds of Present Invention on Activated Immune and APC-Positive Cell Populations A flow cytometry (FACS) was performed to confirm the effect of the methotrexate-peptide compound of the present invention synthesized in Example <1-2> on activated immune and APC-positive cell populations. Specifically, mast cells (Raw264.7) were cultured, and then were treated with the methotrexate-peptide compound of the present invention synthesized in Example <1-2> or methotrexate, LPS (2 μg/mL) used as the stimulant, and the Th17 differentiation-promoting cytokines TGF-β, and IL-23 (20 ng/mL respectively). After 24 hours, the cells were treated with antibodies specific for the mast cell differentiation markers CD11b and CD86 for 30 minutes, and then washed twice with PBS and FACS analysis was performed.

As a result, it was confirmed that the compound having a structure in which methotrexate and a peptide are connected to each other via covalent bond according to the present invention could remarkably reduce the number of CD11b$^+$/CD86$^+$ cell populations, compared to methotrexate (FIG. 6).

Experimental Example 7. Effect of Compounds of Present Invention on Expression of Inflammatory Cytokines A enzyme-linked immunosorbent assay (ELISA) was performed to confirm the effect of the methotrexate-peptide compound of the present invention synthesized in Example <1-2> on IL-17A and IFN-γ secretion in splenocytes. Specifically, splenocytes were isolated from 6-7 week old mice as described in Experimental Example 2 above, and then were treated with the methotrexate-peptide compound of the present invention synthesized in Example <1-2> or methotrexate, LPS (2 μg/mL) used as the stimulant, and the Th17 differentiation-promoting cytokines TGF-β, and IL-23 (20 ng/mL respectively). After 48 hours, ELISA kits (R & D) specific for the secretion markers IL-17A and IFN-γ upon Th17 differentiation were used to perform absorbance measurements (Spectramax M2, Molecular Devices).

As a result, it was confirmed that the compound having a structure in which methotrexate and a peptide are connected to each other via covalent bond according to the present invention could remarkably reduce the secretion of the inflammatory cytokines IFN-γ and IL-17A, compared to methotrexate (FIG. 7).

Experimental Example 8. Inhibitory Effect of Compounds of Present Invention on MMP Activity The effect of the methotrexate-peptide compound of the present invention synthesized in Example <1-2> on MMP activity induced by TNF-α and IL-17 was confirmed. Specifically, the HaCaT keratinocytes were cultured, and then the cells were pretreated with 5, 10, or 100 μM methotrexate-peptide compound of the present invention or methotrexate, and 30 minutes later, treated with TNF-α and IL-17 as a stimulant. The culture broth was collected after 48 hours of culture, and the culture broth and the zymography buffer (4% SDS, 0.01% bromophenolblue, 20% glycerol, 0.125 M Tris-Cl (pH 6.8)) (Sigma) were reacted in a 1:1 ratio, and then 20 μl of the reaction solution was electrophoresed on 8% sodium dodecylsulfate-polyacrylamide gel electrophoresis (SDS-PAGE) (10% gelatin). Thereafter, the gel was washed three times for 10 minutes in 0.1% Triton X-100 (Daejung Chemicals & Metals Co. LTD) buffer, activated in TNCB (50 mM Tris (pH7.5), 150 mM NaCl, 10 mM CaCl$_2$/D.W) (Sigma-Aldrich) buffer, and stained with Coomassie blue, and then the intensity of the band was measured.

As a result, it was confirmed that the compound having a structure in which methotrexate and a peptide are connected to each other via covalent bond according to the present invention could more remarkably reduce the expression of MMP-9 and MMP-2 genes even at a much lower concentration, compared to methotrexate (FIG. 8).

Preparation Example 1. Preparation of Pharmaceutical Composition

<1-1> Preparation of Powder

| Methotrexate peptides of the present invention | 2 g |
|---|---|
| Lactose | 1 g |

The above ingredients were mixed, and then filled in airtight packs, thereby preparing a powder.

<1-2> Preparation of Tablet

| Methotrexate peptides of the present invention | 100 mg |
|---|---|
| Corn starch | 100 mg |
| Lactose | 100 mg |
| Magnesium stearate | 2 mg |

The above ingredients were mixed, and then tableted according to the conventional method for producing tablets, thereby preparing a tablet.

<1-3> Preparation of Capsule

| Methotrexate peptides of the present invention | 100 mg |
|---|---|
| Corn starch | 100 mg |
| Lactose | 100 mg |
| Magnesium stearate | 2 mg |

The above ingredients were mixed, and then filled in a gelatin capsule according to the conventional method for producing capsules, thereby preparing a capsule.

<1-4> Preparation of Pill

| Methotrexate peptides of the present invention | 1 g |
|---|---|
| Lactose | 1.5 g |
| Glycerin | 1 g |
| Xylitol | 0.5 g |

The above ingredients were mixed, and then brought to 4 g per pill according the conventional method, thereby preparing a pill.

<1-5> Preparation of Granule

| Methotrexate peptides of the present invention | 150 mg |
|---|---|
| Soybean extract | 50 mg |
| Glucose | 200 mg |
| Starch | 600 mg |

The above ingredients were mixed, and then 100 mg of 30% ethanol was added thereto and the mixture was dried at 60° C. to form a granule, and then the granule was filled in packs.

<1-6> Preparation of Injectable Solution

| Methotrexate peptides of the present invention | 10 μg/ml |
|---|---|
| Dilute hydrochloric acid BP | until it reaches pH 3.5 |
| Sodium chloride for injection BP | maximum 1 ml |

The TRPV1 inhibitory peptide of the present invention was dissolved in an appropriate volume of sodium chloride for injection BP, and the pH of the resultant solution was adjusted to pH 3.5 by using dilute hydrochloric acid BP, and then the volume was adjusted by using sodium chloride for injection BP and the solution was mixed sufficiently. The solution was filled in a 5 ml Type I ampoule made of transparent glass, and the glass was melted to seal the ampoule under the upper grid of air, and then the ampoule was sterilized by autoclave at 120° C. for at least 15 minutes, thereby preparing an injectable solution.

INDUSTRIAL AVAILABILITY

The compound having a structure in which methotrexate and a peptide are connected via a covalent bond according to the present invention has excellent physiological activity such as anti-cancer or anti-inflammatory action and has markedly reduced toxicity with respect to cells, and thus, can be applied to various industrial fields such as medicines.

SEQUENCE LIST TEXT

SEQ ID NO: 1:
Arg Phe Leu Lys Arg Leu Asp Arg Asn Leu Trp

SEQ ID NO: 2:
aacatccaac cttcccaaac g

SEQ ID NO: 3:
gaccctaagc ccccaattct c

SEQ ID NO: 4:
atcattcacc aggcaaattg c

SEQ ID NO: 5:
ggcttcagca taaagcgttt g

SEQ ID NO: 6:
ttcgacacat gggataacga

SEQ ID NO: 7:
tctttcaaca cgcaggacag

SEQ ID NO: 8:
ggtcaacctc aaagtcttta actc

SEQ ID NO: 9:
ttaaaaatgc aagtaagttt gctg

SEQ ID NO: 10:
agcgggacat atgaatctac taagaga

SEQ ID NO: 11:
gtcctagtag ggaggtgtga agttg

SEQ ID NO: 12:
cctcttctat ccaaccagta tc

SEQ ID NO: 13:
ctccgcttca taactgtgt

SEQ ID NO: 14:
gaaggcatcc agacccgaaa c

SEQ ID NO: 15:
acccatggcg gtgaccatgc

SEQ ID NO: 16:
gaaggcatcc agacccgaaa c

SEQ ID NO: 17:
acccatggcg gtgaccatgc

SEQ ID NO: 18:
tgcccacctt tcctcccagc aa

SEQ ID NO: 19:
ccgggtctga cggctcgaag

SEQ ID NO: 20:
tggacgtgaa gacgcggctg g

SEQ ID NO: 21:
gatttggcgg ctggaggagg tc

SEQ ID NO: 22:
ctaaagtgcg tctgcta

SEQ ID NO: 23:
tgggtgctca gatggtata

SEQ ID NO: 24:
ctgctggagg gcgaggaatg c

SEQ ID NO: 25:
ccaccgaggc caccgccata

SEQ ID NO: 26:
aggtccataa taggcatgat

SEQ ID NO: 27:
caaggacaga aactcagaaa

SEQ ID NO: 28:
atttccatgc cgtctacagg

SEQ ID NO: 29:
gcccagtaac tcagctactc

SEQ ID NO: 30:
gtcgcagctg gaacgcaaca

SEQ ID NO: 31:
cctggcctcc tgattagtgg

SEQ ID NO: 32:
cctctctaag ggtgagctga

SEQ ID NO: 33:
ctgggttttg gtgagggaaa

The invention claimed is:

1. A compound having a structure in which methotrexate and a peptide are connected via a covalent bond, wherein the peptide is a peptide having the amino acid sequence consisting of SEQ ID NO: 1.

2. The compound according to claim 1, wherein the peptide is a water-soluble peptide.

3. An anti-cancer or anti-inflammatory pharmaceutical composition comprising the compound of claim 1.

4. The pharmaceutical composition according to claim 3, having the formulation selected from the group consisting of a powder, a granule, a tablet, a capsule, a suspension, an emulsion, a syrup, an external preparation, a suppository, and a sterile injectable solution.

* * * * *